(12) United States Patent
Nilsson

(10) Patent No.: US 7,345,274 B2
(45) Date of Patent: Mar. 18, 2008

(54) METHOD FOR PERFORMING IN VIVO DOSIMETRY

(76) Inventor: Görgen Nilsson, Gryningsvägen 47, S-743 32, Storvreta (SE)

(*) Notice: Subject to any disclaimer, the term of this patent is extended or adjusted under 35 U.S.C. 154(b) by 225 days.

(21) Appl. No.: 10/513,240

(22) PCT Filed: May 6, 2003

(86) PCT No.: PCT/SE03/00725

§ 371 (c)(1),
(2), (4) Date: Dec. 17, 2004

(87) PCT Pub. No.: WO03/092813

PCT Pub. Date: Nov. 13, 2003

(65) Prior Publication Data

US 2005/0151071 A1    Jul. 14, 2005

(30) Foreign Application Priority Data

May 6, 2002    (SE)    .................... 0201371

(51) Int. Cl.
*G12B 13/00* (2006.01)
*G01D 18/00* (2006.01)

(52) U.S. Cl. .................... 250/252.1; 378/207

(58) Field of Classification Search ............ 250/252.1, 250/484.5, 363.09, 363.1; 378/207, 65, 151
See application file for complete search history.

(56) References Cited

U.S. PATENT DOCUMENTS

| | | | | |
|---|---|---|---|---|
| 5,334,851 A | * | 8/1994 | Good et al. | 250/582 |
| 5,533,508 A | * | 7/1996 | Doiron | 600/317 |
| 5,635,709 A | * | 6/1997 | Sliski et al. | 250/252.1 |
| 5,757,021 A | * | 5/1998 | Dewaele | 250/581 |
| 5,769,779 A | * | 6/1998 | Alderson | 600/1 |
| 5,818,902 A | * | 10/1998 | Yu | 378/65 |
| 5,844,241 A | * | 12/1998 | Liu et al. | 250/363.04 |
| 5,938,605 A | * | 8/1999 | Hasing et al. | 600/436 |
| 6,047,257 A | * | 4/2000 | Dewaele | 704/270 |
| 6,225,622 B1 | * | 5/2001 | Navarro | 250/252.1 |

(Continued)

FOREIGN PATENT DOCUMENTS

DE    19907774 A1    8/2000

OTHER PUBLICATIONS

Webb, Jac et al. "A preliminary investigation of radiation dose reduction on an EMI CT5005 whole body scanner using a copper wedge." IN: British Journal of Radiology, 1982, No. 55, pp. 634-639.

(Continued)

*Primary Examiner*—Dave Porta
*Assistant Examiner*—Faye Boosalis
(74) *Attorney, Agent, or Firm*—Pearne & Gordon LLP

(57) ABSTRACT

The present invention relates to a method enabling quantification of dose delivery in radiotherapy treatment during patient-specific treatment of the patient utilizing measurements in predefined time-intervals with information means positioned in the radiation beam, between the patient and the source and converting the readings to corresponding measures in a phantom. The invention additionally covers the method to obtain the said calibration factors for the detectors. The said calibration factors are obtained for each information means, field and said definable time-interval simultaneously irradiating the information means and said phantom including detectors to measure the absorbed dose using the said patient-specific treatment without patient.

28 Claims, 3 Drawing Sheets

U.S. PATENT DOCUMENTS

| | | | |
|---|---|---|---|
| 6,271,536 B1* | 8/2001 | Buytaert et al. | 250/584 |
| 6,298,115 B1* | 10/2001 | Nilsson | 378/65 |
| 6,364,529 B1* | 4/2002 | Dawson | 378/207 |
| 6,493,574 B1* | 12/2002 | Ehnholm et al. | 600/429 |
| 6,594,336 B2* | 7/2003 | Nishizawa et al. | 378/65 |
| 6,697,452 B2* | 2/2004 | Xing | 378/69 |
| 6,714,620 B2* | 3/2004 | Caflisch et al. | 378/65 |
| 6,800,870 B2* | 10/2004 | Sayag | 250/584 |
| 6,811,079 B1* | 11/2004 | Vraa et al. | 235/383 |
| 6,904,162 B2* | 6/2005 | Robar et al. | 382/128 |
| 6,907,105 B2* | 6/2005 | Otto | 378/65 |
| 6,945,713 B2* | 9/2005 | Vraa et al. | 396/511 |
| 7,024,026 B1* | 4/2006 | Ritt et al. | 382/128 |
| 7,095,034 B2* | 8/2006 | Haug et al. | 250/484.4 |
| 2002/0012999 A1* | 1/2002 | Madsen et al. | 436/8 |
| 2002/0106054 A1* | 8/2002 | Caflisch et al. | 378/65 |
| 2003/0068009 A1* | 4/2003 | Xing | 378/65 |
| 2005/0010110 A1* | 1/2005 | Black et al. | 600/436 |
| 2005/0197564 A1* | 9/2005 | Dempsey | 600/411 |
| 2006/0017009 A1* | 1/2006 | Rink et al. | 250/484.5 |
| 2006/0027756 A1* | 2/2006 | Thomson et al. | 250/370.07 |
| 2006/0203967 A1* | 9/2006 | Nilsson | 378/207 |
| 2006/0219945 A1* | 10/2006 | Jaradet | 250/492.1 |

OTHER PUBLICATIONS

Axelsson, B et al. "Evaluation of radiation exposure to personnel in cardiac angiography." IN: Radiation Protection Dosimetry, 1995, vol. 57, No. 1-4, pp. 433-436.

Booz, J et al. "Neutron absorbed dose measurements in phantom from 252-CF source." IN: Sixth Symposium on Microdosimetry, Brussels, Belgium, May 22-26, 1978, vol. 1, ISBN: 0 906346 02 9, pp. 515-533.

* cited by examiner

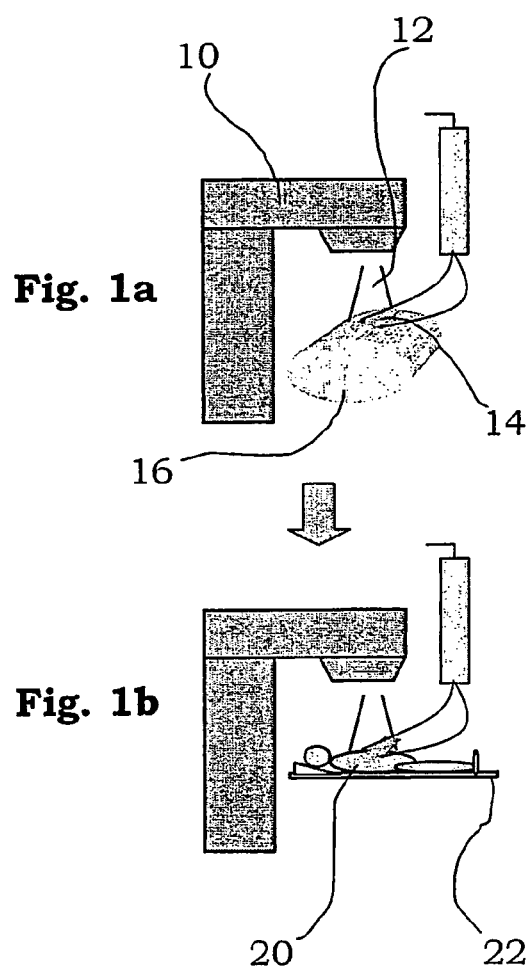
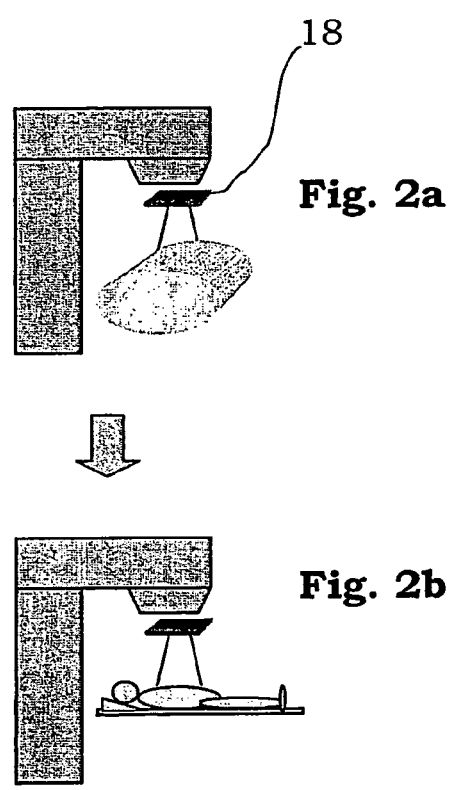
Fig. 1a
Fig. 1b
Fig. 2a
Fig. 2b

1. Patient anatomy data (CT, MR, PET) and images
2. Treatment planning on patient
3. Apply treatment plan on phantom (surrogate patient) as a plan in the computer
4. "Treat" identical phantom with patient specific plan and measure the distribution
5. Compare the planned and the measured data
6. Archive data in patient database

METHOD FOR PERFORMING IN VIVO DOSIMETRY

TECHNICAL FIELD

The present invention relates to a method for calibrating detectors intended for use in an apparatus for radiotherapy during treatment of a patient to verify the accuracy of the delivered dose to the patient.

BACKGROUND OF THE INVENTION

Radiotherapy has been used to treat cancer in the human body since early 1900. Even though radiation of cancer tumours is known to be efficient, mortality rate for many cancers remained virtually unchanged for a long time. The major reasons for this have been the inability to control the primary tumour or the occurrence of metastases. Only by improving the local control may the treatment be more effective. In the last years Treatment Planning Systems, TPS, in Radiation Therapy have developed extensively and is now able to take into account the anatomy of the specific patient and in a time efficient way plan a more optimised treatment for each individual patient, homogenous dose to the target and minimum dose to risk-organs.

The treatment technique to deliver this optimised treatment is more complicated than conventional treatments because each field must be modulated laterally in intensity and thereby compensate for the heterogeneity and contour of the patient, the technique is called IMRT—Intensity Modulated Radiation Therapy. The delivery can be done using compensators, filters that reduce the intensity to a predefined level in each part of the field due to attenuation of the primary photon beam. However when using several fields (4-8), each field requiring individual compensators, this technique is time consuming and requires a lot of effort. Additionally the attenuation of the beam also causes unwanted change of the spectral distribution in the beam, thereby complicating the whole process. The most common way to deliver the IMRT fields will therefore be to use the MLC (Multi Leaf Collimator) a device that consists of thin blocks (Leafs) that can be individually positioned to block a small part of the field and thereby shape the beam in the lateral direction to various irregular shapes. By moving the Leafs during the treatment each part of the treated volume will be irradiated during various time and thereby the intensity over the treated area is modulated.

The new treatment technique however impose that the patient is exactly in the position expected, something not always easy to achieve. Additionally the requirements on accurate dose delivery increase and thereby the requirements on quality control (QC) of the treatment machine, the planning process and finally during the treatment, increase. New verification and QC are to be used. However very little has been published on measurements during treatment, In Vivo dosimetry.

Traditional In Vivo dosimetry, measuring with a detector on the skin of the patient to predict the dose inside the patient is very demanding already with a fixed field (conventional therapy) due to limitations in the TPS (Treatment Planning System) to predict the dose distribution in the region of the patient where externally generated secondary electrons contribute significantly to the delivered dose e.g. build-up region (the part where the beam enters the patient and to a depth 5-35 mm into the patient). Thereby neither the surface or skin dose or the dose in air up-streams the patient can be accurately predicted by the TPS in fixed fields and the difficulty increases with a dynamically delivered treatment. In fixed fields this is solved either by using a special design of the detector, by general calibration or a combination of the two. In IMRT treatments it is not that easy to handle this either by general calibration or design due to the fact that the varying intensity in the field is patient specific. The traditional In Vivo dosimetry is normally not used at each fraction and thereby the perturbation of the specially designed detectors becomes negligible. The small margins in IMRT treatments require extended dosimetry and quality control also at each fraction to minimise the uncertainties and therefore the perturbation of the detectors used in conventional therapy becomes significant. Additionally when using IMRT, measurements must be done in many points to verify the field's topography and the lateral position of the detectors is very critical. To simplify the problem it has been suggested to just measure the fluence in air. However, then the discrepancy from the predicted values will be difficult to judge due to lack of understandable quantification.

Alternatively to traditional in vivo dosimetry it has been proposed to use imaging systems positioned down-streams the patient, film or EPID (Electronic Portal Imaging Device) where the device is calibrated to measure dose. Such a method is discussed in "Portal dose image prediction for dosimetric treatment verification in radiotherapy I: and algorithm for open beam", by K. I. Pasma et al., Medical Physics 25(6), pages 830-840, 1998. A comparison can then be done with calculated dose distribution using e.g. the TPS (Treatment Planning System) at the position of the measuring device. An example of this is described in "In Vivo dosimetry for prostate cancer patients using an electronic portal imaging device; demonstration of internal organ motion", by M. Kroonwijk et al., Radiotherapy and Oncology. 49(2), pages 125-132, 1998. Another alternative is to calculate the dose distribution in the patient from the measured dose distribution in the EPID. This is disclosed in "Modelling the dose distribution to an EPID with collapsed cone kernel superposition", C. Vallhagen Dahlgren et al., Workshop in Uppsala, Mar. 13, 2001, organised by the company MDS Nordion.

The latter has the benefit of providing data that is more easily understandable. However measurement down-streams the patient alone will always be less accurate than combined with measurements up-streams the patient and will thereby not distinguish if the deviation was caused due to incorrect dose delivery by the treatment machine or due to positioning errors or change in anatomy of the patient (the patient might loose weight etc. from original diagnostics). The latter is important not least in order to analyse the root of the deviation and thereby to prevent it from occurring in the next treatment-fraction (normally a patient receives 30 fractions before the treatment is completed).

BRIEF DESCRIPTION OF THE INVENTION

The aim of the present invention is to separate the dose verification from the patient-positioning verification during Radio Therapy treatment of a patient and provide a method to perform the dose verification. The invention is thereby a method to calibrate the detectors to be used In Vivo (during treatment) in a time-efficient and accurate way to achieve high quality, reliable dose measurements during treatment.

This aim is achieved by a method characterised by claim 1. Preferable embodiments of the invention are characterised by the dependent claims.

According to one aspect of the invention it is characterised by the steps of irradiation of a phantom, measurement in said phantom, measurement with detectors (ExtDet) between the patient and the radiation source, wherein said measurements are divided in time-intervals, and analysing the measurements for obtaining information regarding the relationship between the measurements in the phantom and between the patient and the treatment source at each time-interval, which information can be used in the treatment of the patient.

According to the invention the relationship between the measurements may be utilised in different ways.

Because the measurements in the phantom and by the detectors are stored in specific time-intervals a proportionality is obtained between the measurements and a fluence reference can be defined. This enables the calculation of calibration factors for the detectors, which are used in the subsequent treatment of the patient, In Vivo measurement.

The readings from such In Vivo measurements shall after applying the calibration factors predict the dose inside a phantom as if it was in place. The quantification of a deviation in dose distribution can thereby be used to judge if the deviation is acceptable or not. In most cases this verification of the dose delivery will be sufficient, providing similar results as the off-line verification.

The verification of the patient positioning can then be done in a traditional way using an EPID or other methods could be used e.g. using a diagnostic x-ray source and transmission detector in a projection out of the treatment beam (called image guided radio Therapy). The use of diagnostic x-ray source would have the benefit of extensive improvement in image-contrast and thereby position accuracy, as is well known in the art.

An alternative may be a fluence verification where a reference value for each time-interval is obtained for the ExtDet comparing the integrated value for all time intervals with an integrated measurement in the phantom. A combination with back projection from the EPID-images or as an input to the treatment planning system could give quantitative dose data in the patient.

After verifying major deviations in dose delivery and/or patient positioning a second step can be to combine the two and thereby predict the dose distribution in the patient for more precise checks of dose to the tumour, risk-organs etc. This data from one fraction or accumulated for several fractions can be used to modify the treatment plan for the remaining treatment fractions and thereby compensate for the earlier deviations. Such an adaptive treatment technology can be updated after each fraction if required.

Another alternative to measure the fluence with the detector up-streams the patient, ExtDet, is to calculate the fluence using any information of the MLC positions as input and then calibrate that fluence using the described method, eg. calibrate the fluence for each time interval to dose measured in the phantom during the pre treatment verification. Such a determination of the dose in the phantom will be limited in accuracy and verification compared to the use of an ExtDet but still very useful because it enables quantification of deviations during treatment as dose in the phantom as if it was in place.

These and other aspects of, and advantages with, the present invention will become apparent from the following detailed description and from the accompanying drawings.

BRIEF DESCRIPTION OF THE DRAWINGS

In the following detailed description, reference will be made to the accompanying drawings, of which FIG. 1a schematically shows a treatment machine to which a phantom is arranged, which in turn is provided with detectors, FIG. 1b schematically shows the arrangement of FIG. 1a but with a human body instead of the phantom, FIG. 2a schematically shows the machine of FIG. 1a but with a 2D detector device arranged between the machine and the phantom, FIG. 2b schematically shows the arrangement of FIG. 2a but with a human body instead of the phantom.

DETAILED DESCRIPTION OF THE INVENTION

Figure 3:
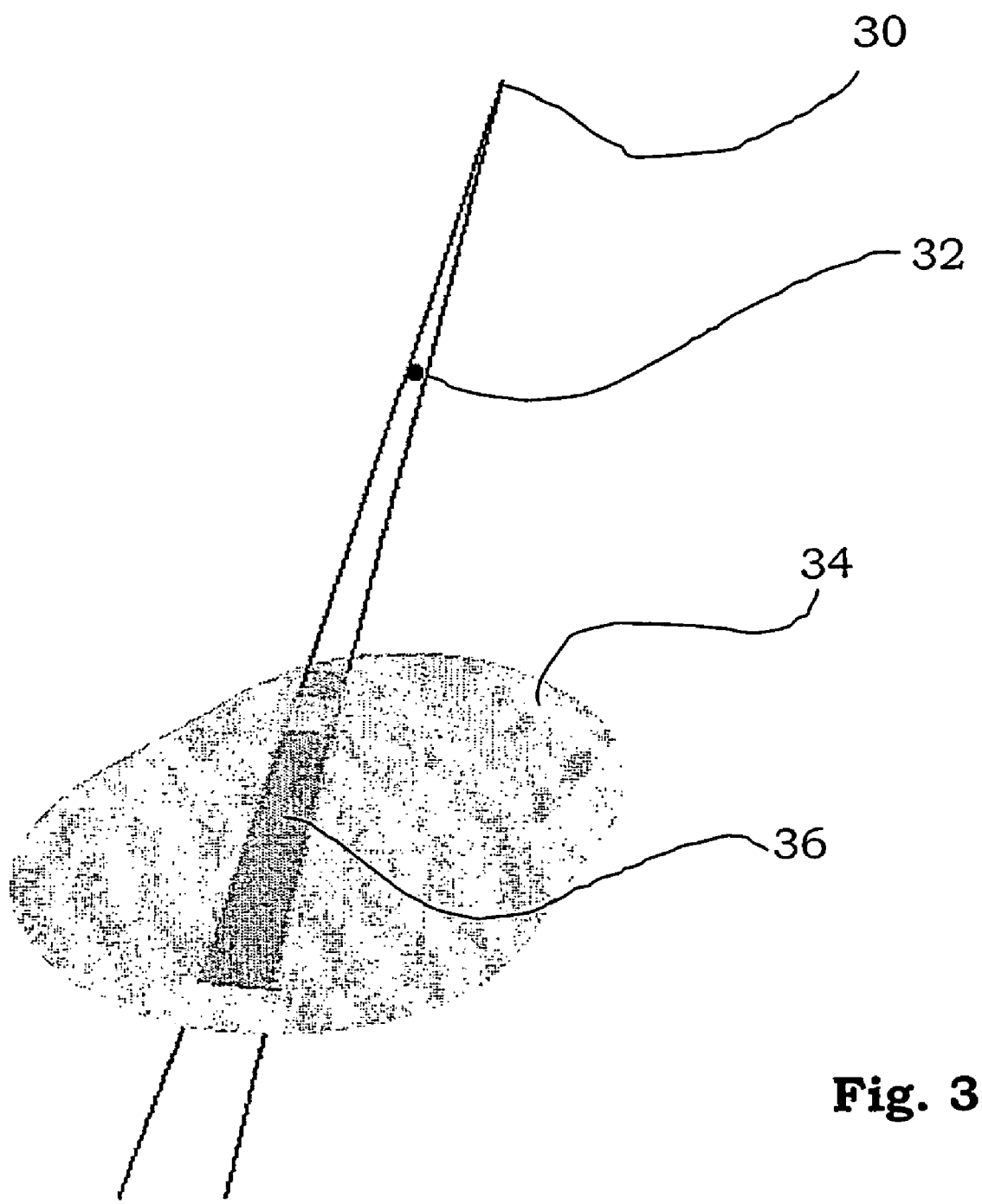
FIG. 3 is a schematic view of a radiation beam.

A radiotherapy device utilised for treating tumours with radiation is shown schematically in FIGS. 1-2 and is generally denoted with reference numeral 10. The device comprises a radiotherapy system capable of emitting a beam 12 of electrons or photons from a treatment head. The radiotherapy system is provided with conventional field-shaping device (not shown), for example an MLC, for allowing the lateral shape of the beam to be altered so as to shield off non-affected areas of the body and concentrate the beam to the tumour. Control means (not shown) are provided for the radiotherapy system.

A table 22 is arranged for a patient 20 to lie on. The table is rotatable around a vertical axis, and movable horizontally and vertically in order to place the area to be treated of the patient in the area of the beam. Further, the method according to the invention utilises different detectors for measuring the radiation emitted from the radiotherapy device. They may for example comprise real-time detectors for measurement on surface skin 14, such as semiconductor detector, gas detector, scintillator detector etc. The detector device might be thin or including a build-up to reduce the dependency on scatter radiation. It might also be designed in a way that it is evenly thick measured in g/cm2 over its entire area thereby taking into account the various density in encapsulation and the detector itself at a typical beam modality.

The detectors may also be detectors for measurement in-between radiation source and phantom/patient like for example imaging systems such as film or EPID. The detectors are connected to suitable signal processing means (not shown). The above mentioned details are well known to the man skilled in the art and will not be described in detail.

The method according to the present invention is aimed at utilising the above-mentioned equipment in order to enable quantification of dose delivery in radiotherapy treatment, in particular during patient-specific treatment of the patient (from now on called In Vivo) utilising measurements in predefined time-interval with detectors (from now on called ExtDet) positioned in the radiation beam, between the patient and the source and converting the readings to corresponding measures in a phantom using the proportionality between the measurements of the detectors and the measures in the phantom.

The method according to the present invention is further aimed at preferably obtaining calibration factors for the ExtDet. The said calibration factors are obtained for each ExtDet per point in the defined segment in the phantom 36, FIG. 3, and said definable time-interval for each field simultaneously irradiating the ExtDet and said phantom including detectors to measure the absorbed dose using the said patient-specific treatment without patient (from now on called off-line).

An example of utilising the method according to the invention may be described with the following steps:

An individual treatment plan for the patient is made using a Treatment Planning System (TPS). The anatomy of the patient is then defined using diagnostic equipment e.g. CT, Computerised Tomography and the radiation characteristics of the treatment device is defined generally by measurements both imported in the TPS. The target-volume and risk-organs are defined and then the optimum plan for the treatment is made where criteria as maximum dose to the risk-organs and the minimum dose to the target etc. is used. The outcome of the plan is information that will be used by the treatment machine to define projections, beam modality, field shapes and movement of the MLC-leaves etc.

The patient specific treatment plan, in the TPS, is applied on a phantom, suitable for dose measurements, and the dose distribution inside the phantom is calculated.

Figure 4:
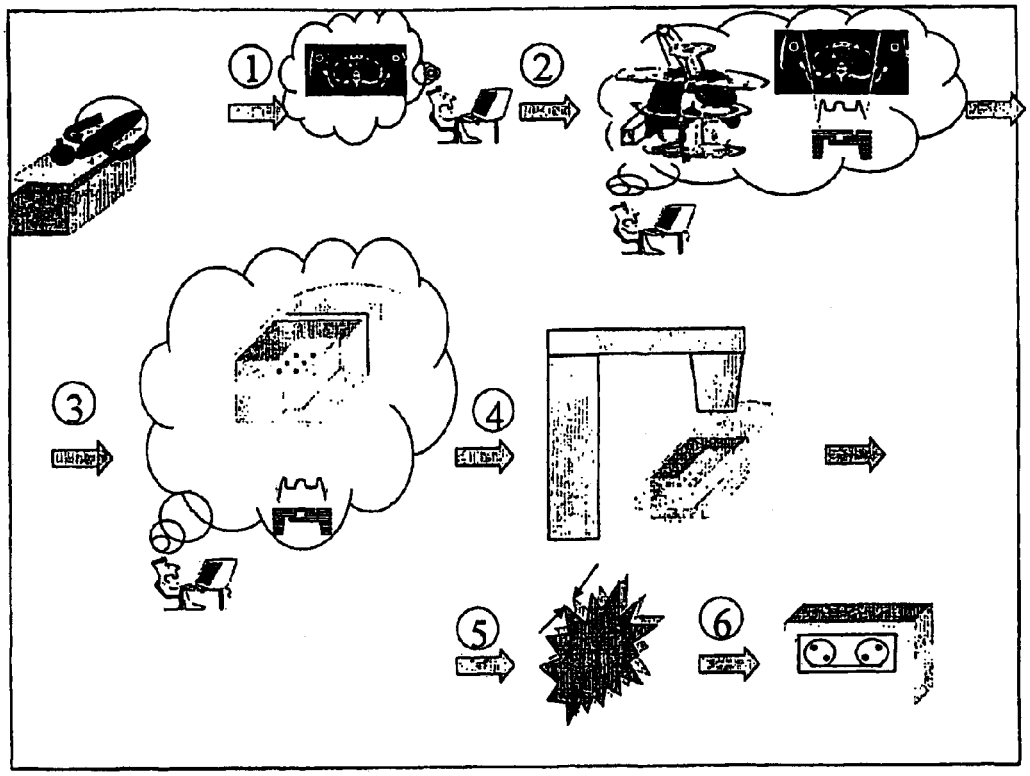
FIG. 4 shows off-line verification of a treatment plan.

Prior to treatment, off-line, a physical phantom, identical to the one used in the calculation, is irradiated using the patient specific treatment. The dose distribution inside the phantom is measured to verify the integrated dose comparing the measurement and the plan for a complete field, sub-field or fraction (off-line quality control or pre treatment verification). Additionally the dose distribution is measured for each field, in all measurement points in the phantom for each time-interval, defined by appropriate time or synchronisation to the treatment machine of the Intensity Modulated field, and stored. The above procedure is shown in FIG. 4.

Simultaneously as measuring inside the phantom, off-line, the dose is also measured using external detectors, ExtDet, on the phantom surface or in any position in the beam between the phantom and the treatment source using the same time-interval as in the phantom measurements or synchronized to it. This step may also be done by first placing detectors inside the phantom and measure the irradiation for each time interval and then to place the detectors upstream the phantom, reproduce the previous irradiation conditions and measure it for each time interval. With this solution the same detectors may be used for both measurements. The obtained reading for each ExtDet, for each field and time-interval and interval will then be used to calculate the calibration factors together with the dose values in the phantom. Either the obtained-readings are firstly stored and subsequently the calibration factors are calculated, or they are calculated immediately. The calibration factors are preferably calculated according to $$Cal_{n,f,seg-n,f,p,t(i),t(i+1)} = S_{n,f,t(i),t(i+1)} / (D_{seg-n,f,p,t(i),t(i+1)}),$$
where D: Absorbed dose measured in the phantom with know shape, positioning and orientation during a certain time interval S: The integrated signal from the ExtDet n: Detector-element in ExtDet, 32 in FIG. 3 f: The specific field (one projection of the beam defined by a field-identity)

seg: A segment in the phantom described as the shadowed volume of one specific detector-element in the ExtDet, n and in one specific projection defined by the field, f, 36 in FIG. 3 p: Well defined point in the segment

Cal: The calibration factor t(i): Time at start of interval i, t(0) is the start time for the sequence.

t(i+1): Time at start of interval i+1, t(T) is the end of the sequence.

$D_{seg-n,f,p,t(i),t(i+1)}$ The dose in point p in the phantom-segment defined by the DetExt detector-element, n and the field (projection), f integrated from time t(i) until t(i+1)

$S_{n,f,t(i),t(i+1)}$ The signal from the ExtDet detector-element, n, in the field, f, integrated from time t(i) until t(i+1)

$Cal_{n,f,seg-n,f,p,t(i),t(i+1)}$ The calibration factor to be used with ExtDet detector-element n, in the field, f. To convert the signal integrated from time t(i) until t(i+1) to achieve the dose in the point p in the phantom-segment defined by the DetExt detector-element, n and the field (projection), f integrated from time t(i) until t(i+1)

During treatment of the patient the reading by each of the ExtDet can now be converted to dose in the points in respectively segment in the phantom, as if it was in place, using the said calibration factors for each time-interval according to $$D_{seg-n,f,p,t(i),t(i+1)} = S_{n,f,t(i),t(i+1)} / Cal_{n,f,seg-n,f,p,t(i),t(i+1)}$$

The readings from all time-intervals for each specific dose point in the phantom can be totalised to present the total dose in that point for each respectively field according to $$D_{seg-n,f,p} = \sum_{i=0 \text{ to } T} D_{seg-n,f,p,t(i),t(i+1)})$$
$$= \sum_{i=0 \text{ to } T} (S_{n,f,t(i),t(i+1)} / Cal_{n,f,seg-n,f,p,t(i),t(i+1)})$$

The dose from all fields to each specific point can then be totalised to present the total dose in all points for the complete treatment fraction (a complete treatment consists of several fractions given over several days or weeks). The total dose in each point can directly be compared with the result from the treatment planning system when applied on the phantom similar to the off-line verification (pre treatment verification).

Deviations between the measured and calculated dose values can be analysed by using the data for each time-interval and thereby simplifying the analysing phase.

If the deviation is caused by incorrect motion of the leaves the calculated dose value in the phantom might be slightly incorrect and in such a case the exact value can be verified using a phantom measurement simulating the motion during the miss-delivered treatment.

The position of the ExtDet can be determined in the transversal plane on the phantom and in particular on the patient using the projection of the detectors or markers well defined to the ExtDet utilising the image from an image device down streams the phantom e.g. EPID or radiographic film.

Incorrect positioning of the patient in the field compared to the detector can be visualised using markers on the detector device that light-up on the EPID image e.g. lead-seeds. Using several projections the positioning of the patient can be defined.

The alternative of a fluence verification of the integrated dose in the phantom with the treatment plan and simultaneously measured reference signals with ExtDet in each time-interval where the $(S_{n,f,t(i),t(i+1)}$ is proportional to the $(D_{seg-n,f,p,t(i),t(i+1)}$ makes it possible to estimate the deviation in fluence for each time-interval during treatment although it is not directly convertible into dose in the phantom.

An alternative to measure the fluence with the detector up-streams the patient, ExtDet, is to calculate the fluence using any information of the MLC positions as input and then calibrate that fluence using the described method, eg. calibrate the fluence for each time interval to dose measured in the phantom during the pre treatment verification. Such a determination of the dose in the phantom will be limited in accuracy and verification compared to the use of an ExtDet but still very useful because it enables quantification of deviations during treatment as dose in the phantom as if it was in place. The information regarding the MLC positions is easily obtainable since there is already provided means in the radio therapy device for controlling the position of the MLC leaves. This information can then be used in the comparison with the measurements inside the phantom.

When using the information of the MLC positions, the calibration factors may be calculated according to $$Cal_{n,f,p,t(i),t(i+1)} = F_{n,f,t(i),t(i+1)} / (D_{f,p,t(i),t(i+1)})$$

where $D_{f,p,t(i),t(i+1)}$ The dose in point p in the phantom at the field (projection), f integrated from time t(i) until t(i+1)

$Fn_{n,f,t(i),t(i+1)}$ The radiation fluency-in the field, f, between the patient and the source along the ray that intersects point p in the phantom integrated from time t(i) until t(i+1)

$Cal_{n,f,p,t(i),t(i+1)}$ The calibration factor describing the relation between the fluency between the patient and the source and the dose in the phantom.

The readings from all time-intervals for each specific dose point in the phantom can be totalised to present the total dose in that point for each respectively field according to $$D_{f,p} = \sum_{i=0 \, to \, T} D_{f,p,t(i),t(i+1)}$$
$$= \sum_{i=0 \, to \, T} F_{n,f,t(i),t(i+1)} / Cal_{n,f,p,t(i),t(i+1)}$$

The method according to the invention may be implemented in the control and measurement system of the radiotherapy device, and thereby using the processor and storage means available there. It may of course be implemented in a stand-alone unit comprising the necessary equipment such as a central processing unit CPU performing the steps of the method according to the invention. This is performed with the aid of a dedicated computer program, which is stored in the program memory. It is to be understood that the computer program may also be run on a general purpose industrial computer instead of a specially adapted computer.

The software includes computer program code elements or software code portions that make the computer perform the method using equations, algorithms, data and calculations previously described. A part of the program may be stored in a processor as above, but also in a ROM, RAM, PROM or EPROM chip or similar. The program in part or in whole may also be stored on, or in, other suitable computer readable medium such as a magnetic disk, CD-ROM or DVD disk, hard disk, magneto-optical memory storage means, in volatile memory, in flash memory, as firmware, or stored on a data server.

It is to be understood that the above description of the invention and the accompanying drawings is to be regarded as a non-limiting example thereof and that the scope of protection is defined by the appended patent claims.

The invention claimed is:

1. Method for enabling quantification of dose delivery in radiotherapy treatment, characterized in that it comprises the steps of
   irradiating a phantom,
   obtaining measurements in said phantom,
   collecting information regarding the irradiation by information means arranged between the phantom and the radiation source, wherein said measurements are divided in time-intervals,
   analysing the measurements, and
   obtaining information regarding the relationship between the measurements in the phantom and the information between the phantom and the treatment source at each time-interval, which relationship information is to be used as verification of the treatment of a patient.

2. Method according to claim 1, characterized in that the information means comprises the position of Multi Leaf Collimator leafs (MLC) arranged for shaping the irradiating beam of the radiation source.

3. Method according to claim 2, characterized in that the measurements in the phantom and a determination of the positions of Multi Leaf Collimator leafs are performed simultaneously.

4. Method according to claim 2 or 3, characterized in, during treatment of the patient, utilising the same positions of the MLC's as during the irradiation of the phantom.

5. Method according to claim 1, characterized in that the information means comprises detectors (ExtDet).

6. Method according to claim 5, characterized in that the measurements in the phantom and with detectors (ExtDet) are performed simultaneously.

7. Method according to any of claims 2 to 6, characterized in calculating calibration factors from the obtained relationship information as the ratio of the reading from information from the information means and the measurements along the radiation ray in the phantom.

8. Method according to any of claims 1 to 6, characterized in the further step of storing the data for each specific time-interval both for measurements in the phantom and information between the patient and the treatment source.

9. Method according to claim 5, characterized in that the detectors (ExtDet) are positioned on the surface of the phantom.

10. Method according to claim 5, characterized in that the detectors (ExtDet) are positioned between the radiation source and the surface of the phantom.

11. Method according to claim 5, wherein the detectors (ExtDet) are placed inside the phantom.

12. Method according to any claims 1 to 6 and 9 to 11, characterized in using a patient specific treatment plan during irradiation of the phantom, and verification of the accuracy of the irradiation of the phantom comparing the measured dose in the phantom with the treatment plan.

13. Method according to claim 5, characterized in, during treatment of the patient, utilising ExtDet in the same lateral positions between the patient and the treatment source as during the irradiation of the phantom.

14. Method according claim 13, characterized in, during treatment of patient, converting the readings from ExtDet to dose using calculated calibration factors for each time-interval.

15. Method according to claim 14, characterized in that the readings are converted according to:

$$D_{seg-n,f,p,t(i),t(i+1)} = S_{n,f,t(i),t(i+1)} / Cal_{n,f,seg-n,f,p,t(i),t(i+1)}.$$

16. Method according to any of the claims 14 to 15, characterized in totalising the readings from all time-intervals for each specific dose point in order to obtain the total dose.

17. Method according to claim 16, characterized in that the totalisation is obtained according to:

$$D_{seg-n,f,p} = \sum_{i=0 \text{ to } T} D_{seg-n,f,p,t(i),t(i+1))} = \sum_{i=0 \text{ to } T} (S_{n,f,t(i),t(i+1)} / Cal_{n,f,seg-n,f,p,t(i),t(i+1)}).$$

18. Method according to claim 5, comprising the further step of determining the position of the ExtDet in the transversal plane using the projection of the detectors or markers well defined to the ExtDet utilising an image from an image device down streams the phantom e.g. EPID or radiographic film.

19. Method according to any of claims 1-6, 9-11, 13-15 and 18, characterized in using the dose distribution in a patient at one treatment fraction or accumulated for several treatment fractions, where the dose distribution is obtained by calculations using measurement of the patient anatomy and delivered dose, to modify the subsequent treatments due to previous treatments in order to adapt the intended dose distribution.

20. Computer program product capable of enabling a computer to perform the method according to any of the claims 1-6, 9-11, 13-15 and 18, wherein at least a portion of said computer program product is stored in a memory of said computer.

21. Computer program product capable of enabling a computer to perform the method according to any of the claims 1-6, 9-11, 13-15 and 18, wherein said computer program product is stored on a computer readable media.

22. Method for enabling quantification of dose delivery in radiotherapy treatment, characterized in that it comprises the steps of
    irradiating of a phantom,
    obtaining measurements in said phantom,
    collecting information regarding the irradiation by information means arranged between the phantom and the radiation source, wherein said measurements are divided in time-intervals, characterized in that the information means comprises detectors (ExtDet),
    analysing the measurements,
    obtaining information regarding the relationship between the measurements in the phantom and the information between the phantom and the treatment source at each time-interval, which relationship information is to be used as verification of the treatment of a patient, and
    calculating calibration factors from the obtained relationship information as the ratio of the reading from information from the information means and the measurements alone the radiation ray in the phantom, characterized in that the calibration factor are calculated according to, $$Cal_{n,f,seg-n,f,p,t(i),t(i+1)} = S_{n,f,t(i),t(i+1)} / (D_{seg-n,f,p,t(i),t(i+1)})$$

where
$D_{seg-n,f,p,t(i),t(i+1)}$ The dose in point p in the phantom-segment defined by the DetExt detector-element, n and the field (projection), f integrated from time t(i) until t(i+1)

$S_{n,f,t(i),t(i+1)}$ The signal from the ExtDet detector-element, n, in the field, f, integrated from time t(i) until t(i+1)

$Cal_{n,f,seg-n,f,p,t(i),t(i+1)}$ The calibration factor to be used with ExtDet detector-element n, in the field, f, to convert the signal integrated from time t(i) until t(i+1) to achieve the dose in the point p in the phantom-segment defined by the DetExt detector-element, n and the field (projection), f integrated from time t(i) until t(i+1).

23. Method according to claim 22, characterized in that the measurements in the phantom and with detectors (Ext-Det) are performed simultaneously.

24. Method for enabling quantification of dose delivery in radiotherapy treatment, characterized in that it comprises the steps of
    irradiating of a phantom,
    obtaining measurements in said phantom,
    collecting information regarding the irradiation by information means arranged between the phantom and the radiation source, wherein said measurements are divided in time-intervals, characterized in that the information means comprises the position of Multi Leaf Collimator leafs (MLC) arranged for shaping the irradiating beam of the radiation source,
    analysing the measurements,
    obtaining information regarding the relationship between the measurements in the phantom and the information between the phantom and the treatment source at each time-interval, which relationship information is to be used as verification of the treatment of a patient, and
    calculating calibration factors from the obtained relationship information as the ratio of the reading from information from the information means and the measurements along the radiation ray in the phantom, characterized in that the calibration factors are calculated according to $$Cal_{n,f,p,t(i),t(i+1)} = F_{n,f,t(i),t(i+1)} / (D_{f,p,t(i),t(i+1)})$$

where
$D_{f,p,t(i),t(i+1)}$ The dose in point p in the phantom at the field (projection), f integrated from time t(i) until t(i+1)

$F_{n,f,t(i),t(i+1)}$ The radiation fluency in the field, f, between the patient and the source along the ray that intersects point p in the phantom integrated from time t(i) until t(i+1)

$Cal_{n,f,p,t(i),t(i+1)}$ The calibration factor describing the relation between the fluency between the patient and the source and the dose in the phantom.

25. Method according to claim 24, characterized in, during treatment of the patient, converting the information from the positions of the MLC's to dose using said calibration factors for each time-interval.

26. Method according to claim 25, characterized in that the readings are converted according to:

$$D_{f,p,t(i),t(i+1)} = F_{n,f,t(i),t(i+1)} / Cal_{n,f,p,t(i),t(i+1)}.$$

27. Method according to any of claims 25-26 characterized in totalising the readings from all time-intervals for each specific dose point in order to obtain the total dose, wherein the totalisation is obtained according to:

$$D_{f,p} = \sum_{i=0 \text{ to } T} D_{f,p,t(i),t(i+1)} = \sum_{i=0 \text{ to } T} F_{n,f,t(i),t(i+1)} / Cal_{n,f,p,t(i),t(i+1)}.$$

28. Method according to claim 24, characterized in that the measurements in the phantom and a determination of the positions of Multi Leaf Collimator leafs are performed simultaneously.

\* \* \* \* \*